US005725833A

United States Patent [19]
Crafton

[11] Patent Number: 5,725,833
[45] Date of Patent: Mar. 10, 1998

[54] WATER BUFFERED ESSENTIAL OILS SMOKELESS INCENSING SYSTEM

[76] Inventor: Richard Crafton, 110 W. Seminary Ave., Lutherville, Md. 21093

[21] Appl. No.: 555,867

[22] Filed: Nov. 13, 1995

[51] Int. Cl.⁶ .................................. A61L 9/03; B05B 1/24
[52] U.S. Cl. ........................ 422/125; 422/5; 422/305; 126/344; D11/131.1; 239/136
[58] Field of Search ...................... D11/131.1; 422/5, 422/305, 125, 126; 239/34, 136; D7/402, 403, 332, 337; 126/344, 363

[56] References Cited

U.S. PATENT DOCUMENTS

| | | | |
|---|---|---|---|
| 14,340 | 3/1856 | Albro | 126/344 X |
| 468,147 | 2/1892 | Berger et al. | 126/344 |
| 611,560 | 9/1898 | Chambers | 422/125 |
| 878,296 | 2/1908 | Loveless | 422/125 |
| 2,077,703 | 4/1937 | Little | 126/344 |
| 5,178,839 | 1/1993 | Spector | 422/5 X |
| 5,197,454 | 3/1993 | Lee | 126/9 R |

*Primary Examiner*—Robert J. Warden
*Assistant Examiner*—Leigh Dawson
*Attorney, Agent, or Firm*—Nikaido, Marmelstein, Murray & Oram LLP

[57] ABSTRACT

A water buffered essential oil non-open flame incensing system including a level fire plate with a metallic fire ring centrally bonded to the upper surface thereof. A stoneware urn is provided having a body portion with a pronounced belly, a bell lip, a throat defined between the body portion and the bell lip, a curved interior surface with a non-flat bottom portion, and an exterior surface. At least the curved interior surface has high fire glazed finish. Water and essential oils to be diffused are filled in the urn and the urn is placed on top of a burning charcoal briquette on the fire ring. Boiling of the water carries the oil in the form of droplets into the atmosphere. The urn is sized to have a small amount of water left at the time the charcoal burns out. A smokeless system may be beneficial for people with smoke allergies.

9 Claims, 3 Drawing Sheets

WATER BUFFERED ESSENTIAL OILS SMOKELESS INCENSING SYSTEM

BACKGROUND OF THE INVENTION

The present invention relates to a system for aromatherapy and, more specifically, to a system for dispensing the aroma of essential oils into a space without the possibility of charring or resinating the oils.

Essential oils are distilled or collected oils of naturally occurring substances. Generally, these have been known for many years. Some examples are oil of eucalytus, oil of peppermint, oil of basil, oil of orange, oil of rosemary, oil of cedarwood, and oil of spearmint. The smell of these oils can be pleasing to some people. An open container can be left standing and a faint amount of the aroma of the oils will spread. There is a difficulty in diffusing the aroma of the oils into a room to a larger degree since the boiling points of these oils is about 172° C.

A previously known device for diffusing essential oils into a room includes an integrally formed shallow open-top ceramic bowl having a cylindrical shell supporting it. The shell has an open front area and an integral base. Water is placed into the bowl, oils are spread upon the water, and a "tea" candle is lit and placed in through the open front area of the shell onto the base to heat the water and oils directly using the open flame.

A difficulty arises in that the candle typically burns for several hours while the water is boiled away after about one half hour. This leaves any remaining oil to be directly heated and actually overheated by the direct action of the flame on the bottom of the bowl. This results in charring and/or resinating of the remaining oil, possibly even causing an undesired odor. A possible fire hazard can be created. The device, being directly heated by the flame, can become untouchable for a long period of time thereby being a direct hazard not only to the knowledgeable user, but also to children and pets. Additionally, because the bowl needs to be positioned at a relatively high level above the flame, a top heavy structure results which can also be a spill hazard. Extremely careful control is required during use.

OBJECTS AND SUMMARY OF THE INVENTION

It is an object of the present invention to provide a water buffered essential oil non-open flame smokeless incensing system which diffuses essential oils into a room without charring or resinating of the oils.

It is a further object of the present invention to provide a water buffered essential oil non-open flame incensing system which avoids the other problems of the known device, while remaining aesthetically pleasing.

The above and other objects are obtained according to the present invention in a water buffered essential oil non-open flame smokeless incensing system which comprises the following structure. A level fire plate has a metallic fire ring centrally bonded to the upper surface thereof. A stoneware urn is provided having a body portion with a pronounced belly, a bell lip, a throat defined between the body portion and the bell lip, a curved interior surface with a non-flat bottom portion, and an exterior surface. At least the curved interior surface has high fire glazed finish.

In use, a conventional charcoal briquette is ignited and placed on the fire ring. The urn filled with water to the throat with the essential oils as desired on top is placed directly on the burning charcoal. The burning time is self-limiting by the charcoal. After about one quarter hour, the water starts to boil and diffuse the oils into the room. The intensity of the diffusion has been surprisingly estimated to be about six to eight times the performance of the previously known device. The charcoal burns out before the water is boiled away. Due to the pronounced belly and the curved interior surface with a non-flat bottom portion, swirling and rolling boiling occurs in the urn which results in far better results than straight boiling. It is believed that a higher degree of turbulence in the water enhances the diffusion of the essential oils. The turbulated boiling is believed to bring the essential oil into smaller and smaller droplets thereby releasing more of the aromatics contained therein. It should be noted that having a flat bottom on the urn will not work.

The fire plate can be high fire stoneware. In addition, the fire plate can have a raised annular outer edge which functions not only as a safety guard from inadvertent touching of the burning charcoal, but also a safety catch in case the urn is knocked over. Plural leg members can be provided on a bottom surface of the fire plate. The leg members are made of hardwood.

The metallic heat ring can have a plurality of radially directed holes to permit additional air to reach the center portion of the burning charcoal. The fire ring functions to hold the burning charcoal up off of the fire plate itself to reduce the possibility of the fire plate becoming too hot to handle or unsafe for the surface it is resting on. Additionally, the fire ring aids in permitting air flow around the entire charcoal briquette.

A metallic chain member can be provided encircling an exterior of the throat of the urn for defining a filling level for the urn and for decorative purposes.

The urn is generally glazed with a high fire finish which is known in the art to be fired at about 2200° C. rather than a low fire finish, known in the art to be fired at about 1800° C. The bell lip of the urn can be unglazed which may result in a desirable residuum of the previously dispersed essential oils being retained and enhancing the current diffusion. The throat of the urn can not be too small or else undesired burbling, splashing and/or a perking effect will occur.

Another embodiment of the present invention is a water buffered essential oil non-open flame incensing system comprising a level fire plate, a metallic stand in the fire plate, a fire net on the fire stand centrally positioned relative to the fire plate, and a stoneware urn, the fire net being sized to hold plural standard charcoal pieces, the urn having a body portion with a pronounced belly, a bell lip, a throat defined between the body portion and the bell lip, a curved interior surface with a non-flat bottom portion, and an exterior surface, with the curved interior surface having high fire glazed finish. This embodiment enables the use of multiple briquettes and a larger quantity of water and essential oils to aromate a larger enclosure.

BRIEF DESCRIPTION OF THE DRAWINGS

The above and other objects and the attendant advantages of the present invention will become readily apparent by reference to the following detailed description when considered in conjunction with the accompanying drawings wherein.

DETAILED DESCRIPTION OF PREFERRED EMBODIMENTS

Figure 1:
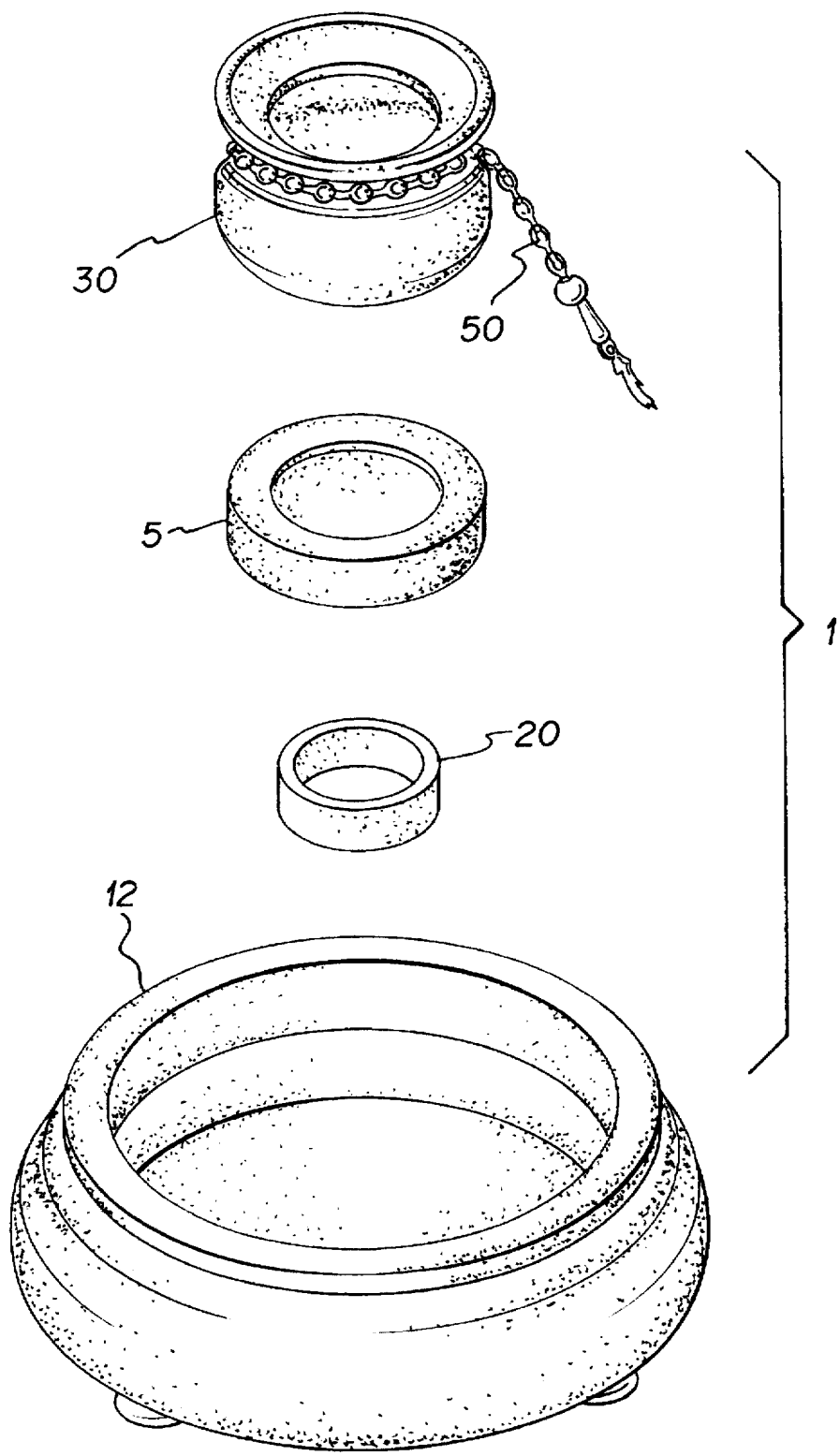
FIG. 1 is an exploded perspective view of the first embodiment of the present invention.
Figure 2:
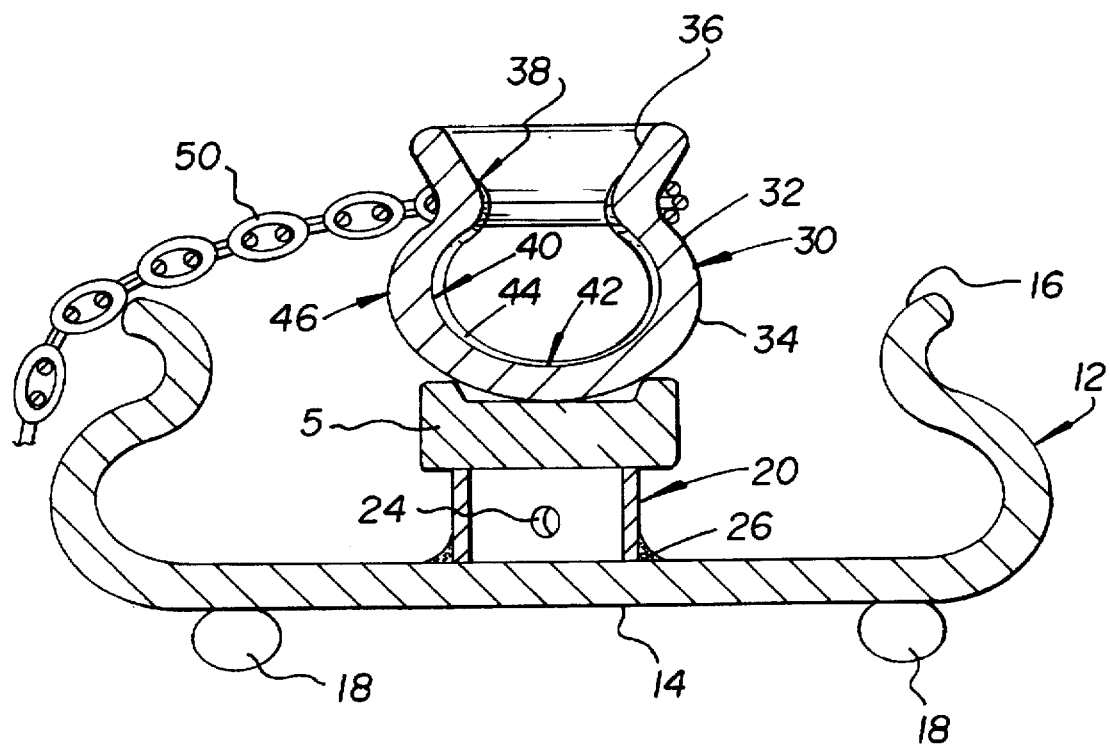
FIG. 2 is a cross-sectional view.

The first embodiment the system 1 for aromatherapy of the present invention is shown in FIGS. 1 and 2 and includes the main components of a level fire plate 12, a metallic fire ring 20 centrally bonded to the fire plate 12 and the stoneware urn 30. In use, charcoal in the form of a briquette S is placed on the fire ring 20 and ignited, and the urn 30 filled with water and essential oils as desired to the line indicated by the chain 50 is placed on top.

The fire plate 12 is made of high fire stoneware having a high fire finish. The plate 12 can have plural leg members 18 fixed to the bottom surface 14 thereof. Preferably, the leg members 18 are hardwood, such as walnut, "chair buttons". They are provided for protecting the surface that the system is resting on from the heat generated by raising the fire plate 12 and providing for an insulating layer of air under the plate. Pine or softwood is totally unsuitable and would tend to ash from the heat. Generally, white wood glue, such as ELMER'S GLUE is suitable for fixing the leg members 18 to the fire plate 12.

The fire plate 12 preferably has a raised annular outer edge 16 provided as a safety catch should the urn 30 be knocked over during use.

The metallic fire ring 20 is centrally bonded at 26 to the fire plate. Any non-toxic, metal-to-ceramic glue would be suitable, such as WELDBOND by Frank T. Ross & Sons, Inc. of Spring Grove, Ill. The fire ring 20 can be simply made by cutting off a suitable piece of copper piping. A typical size is a ⅝ inch long piece of 1 inch diameter pipe. Plural radial holes 24 can be provided for improved air circulation under the burning charcoal. These holes can be ¼ inch in size.

The urn 30 is made of high fire stoneware. It is critical that at least the interior 40 of the urn 30 be glazed with a high fire finish 44. This seals the stoneware. Both the interior surface 40 and the exterior surface 46 can be glazed. It should be noted that the thickness of the stoneware cannot be too thick or else the water inside will not boil. Charcoal burns at a temperature of about 375°–400° F. The body portion 32 of the urn 30 has a pronounced belly 34 which helps define the curved interior surface 40 having a non-flat bottom portion 42. This convexed bottom portion 42 is key to operation of the present invention. A flat interior bottom will not work as well. It is believed that the curved interior surface 40 enables the water to swirl rollingly. Straight boiling as in a flat bottom pot is not as effective. Straight sides to the urn 30 are not as effective. The "turbulated" boiling generated by the particular shape of the interior of the urn 30 brings the essential oils into smaller and smaller droplets thereby releasing more of the aromatics to be carried out of the system by the water vapor from the boiling water.

The urn 30 has a bell lip 36 extending out from the body portion 32 with a throat 38 being defined between the body portion 32 and the lip 36. The throat 38 can not be too small or else undesired burbling, splashing and/or a perking effect will occur. A wide bell lip 36 is desirable to catch small splashes that occur during the boiling of the water. In addition, the bell lip 36 also serves as a platform for the essential oils to vaporize.

A metallic chain member 50 can encircle the throat 38. This chain 50 serves to mark the filling level for the urn 30 so that a user can repeatedly have the same effects from the system. That is, the urn 30 is filled with water to the imaginary line in the throat 38 defined by the chain 50 and then adds several droppers full of the essential oils desired.

The system 1 of the present invention uses charcoal briquettes 5 for the heating. The briquettes 5 are known dehydrated low fire kiln dried pine wood charcoal compacted with potassium nitrate and sulfur to provide for ignition. These are commonly used for liturgical purposes and a typical suitable briquette can be one made by THREE KINGS. The urn 30 rests directly on the burning charcoal. Due to the size of the briquette 5, the amount of burning time and consequently the amount of time for the water to boil is self-limiting. Generally, these briquettes last about 30–35 minutes. The urn is sized such that it will The use of charcoal which has such relatively low burning temperature for heating the water, not only eliminates the express danger of an open flame, but also permits the urn 30 to be picked up by the bell lip 36 during use.

Figure 3:
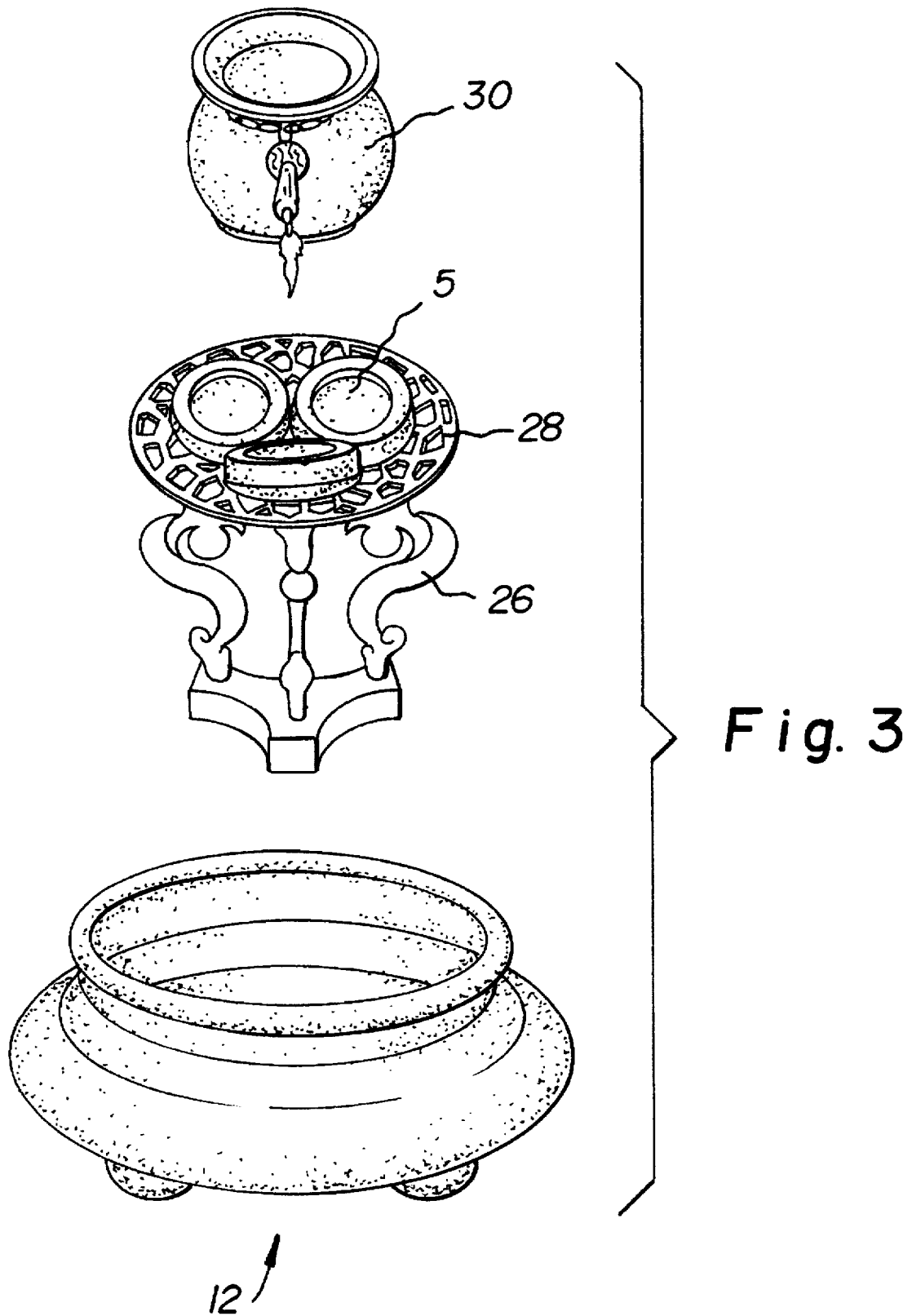
FIG. 3 is an exploded perspective view of the second embodiment of the present invention.

A second embodiment of the present invention is shown in FIG. 3. Although larger in size, the urn 30, and the fire plate 12 are essentially identical to those of the first embodiment. The second embodiment has a metallic stand 26 with a fire net 28 thereon. The stand 26 with the fire net 28 are centrally positioned relative to the fire plate 12. The fire net 28 can be made of stock expanded metal galvanized steel. The stand 26 can be brass. The fire net 28 is sized to hold three standard size charcoal briquettes 5. An ash plate can be provided on the fire plate 12 to catch the ashes from the burning charcoal to make clean up of the system simpler. The urn 30 of this embodiment is also sized to hold sufficient water for 35–40 minutes worth of boiling. In this manner, charring or resinating of the remaining essential oils is avoided.

It is readily apparent that the above-described has the advantage of wide commercial utility. It should be understood that the specific form of the invention hereinabove described is intended to be representative only, as certain modifications within the scope of these teachings will be apparent to those skilled in the art.

Accordingly, reference should be made to the following claims in determining the full scope of the invention.

What is claimed is:

1. A water buffered essential oil non-open flame incensing system comprising a horizontal fire plate, a metallic fire ring bonded to a center of said fire plate; and a stoneware urn removable positioned upon a standard charcoal piece placed on said fire ring, said urn having a body portion with a rotund belly, a bell lip, a throat defined between said body portion and said bell lip, a continuously curved interior surface with no flat bottom portion, and an exterior surface, said curved interior surface having high fire glazed finish.

2. The system of claim 1, wherein said fire plate is high fire stoneware.

3. The system of claim 1, further comprising a metallic chain member encircling an exterior of said throat and defining a filling level for said urn.

4. The system of claim 1, wherein said metallic heat ring has a plurality of radially directed holes.

5. The system of claim 1, further comprising plural leg members on a bottom surface of said fire plate.

6. The system of claim 5 wherein said leg members are made of hardwood.

7. The system of claim 1, wherein said fire plate has a raised annular outer edge.

8. The system of claim 1, wherein said bell lip is unglazed.

9. A water buffered essential oil non-open flame incensing system comprising a horizontal fire plate, a metallic stand in said fire plate, a fire net on said fire stand centrally positioned relative to said fire plate, and a stoneware urn removably positioned upon at least one standard charcoal piece placed on said fire net, said fire net being sized to hold plural standard charcoal pieces, said urn having a body portion with a rotund belly, a bell lip, a throat defined between said body portion and said bell lip, a continuously curved interior surface with no flat bottom portion, and an exterior surface, said curved interior surface having high fire glazed finish.

* * * * *